United States Patent [19]

Bonati

[11] Patent Number: 5,241,972
[45] Date of Patent: Sep. 7, 1993

[54] METHOD FOR DEBULKING TISSUE TO REMOVE PRESSURE ON A NERVE

[75] Inventor: Alfred O. Bonati, New Port Richey, Fla.

[73] Assignee: Meditron Devices, Inc., Hackensack, N.J.

[21] Appl. No.: 695,633

[22] Filed: May 3, 1991

[51] Int. Cl.⁵ ............................................. A61B 17/00
[52] U.S. Cl. ...................................... 128/898; 606/2; 606/13; 606/53
[58] Field of Search .................. 128/68, 68.1, 898; 604/19, 28, 49, 51, 93, 104, 158, 161, 164, 167, 173, 174, 178; 606/2, 13, 15, 14, 16, 53, 60, 61, 79, 82, 83, 84, 99, 100, 105, 167, 170, 179, 180

[56] References Cited

U.S. PATENT DOCUMENTS

| | | | |
|---|---|---|---|
| 4,449,532 | 5/1984 | Storz | 128/4 |
| 4,573,448 | 3/1986 | Kambin | 128/898 |
| 5,041,120 | 8/1991 | McColl et al. | 606/99 |
| 5,158,543 | 10/1992 | Lazarus | 606/191 |

*Primary Examiner*—Stephen C. Pellegrino
*Assistant Examiner*—Jeffrey A. Schmidt
*Attorney, Agent, or Firm*—Joseph C. Mason, Jr.; Ronald E. Smith

[57] ABSTRACT

An arthroscopic method for debulking tissue and a kit of arthroscopic tools for performing the steps of the method. A protruding piece of tissue that is bearing against a nerve is undermined by the formation of a cavity beneath it, and the cavity is collapsed by heat generated by a laser. When the cavity collapses, the protruding tissue falls into it and separates from the nerve. The kit includes plural dilator tubes that are used to progressively dilate the arthroscopic incision and plural cutter tubes that are used in sequence to cut larger and larger pieces of tissue. Plural forceps are employed to remove the cut tissue to form the cavity, and impactor members in the kit are used to compact the bone that surrounds the cavity just before the laser is introduced into the cavity to collapse it.

14 Claims, 5 Drawing Sheets

METHOD FOR DEBULKING TISSUE TO REMOVE PRESSURE ON A NERVE

TECHNICAL FIELD

This invention relates, generally, to surgical procedures and tools having utility in performing those procedures. More particularly, it relates to arthroscopic procedures and tools for removing a bulge on a piece of tissue to relieve pressure on a nerve caused by said bulge.

BACKGROUND ART

Lumbago may be caused by a tissue bulge that extends radially outward from a vertebrae and presses against the lumbar nerve. The condition is treated by surgically removing the bulge.

There are a number of other conditions that have similar origins, i.e., a nerve pinched by a piece of protruding tissue.

The method most often used to remove the offending tissue is to attack it with cutting devices; since the protruding tissue is immediately adjacent a nerve, care must of course be taken to avoid imparting trauma to the nerve.

The incision required to expose the protruding tissue may be large if the tissue removal is accomplished by conventional surgical techniques. However, where arthroscopic surgical techniques are used, the incision can be quite small. Still, arthroscopic surgeons are currently removing the tissue by attacking it with various cutting instruments; thus, the patient is spared the large incision, but the success of the procedure still depends on how much tissue is removed without damaging the nerve.

Since the advent of arthroscopy, the making of large incisions where such incisions are not needed has become an unacceptable practice. The short post-operative recovery periods made possible by arthroscopic techniques as well as the fact that many of such techniques can be performed on an out-patient basis makes arthroscopic procedures the procedures of choice for knowledgeable patients. Still, virtually all arthroscopic surgeons perform tissue-removal surgery by following the same cutting techniques used by nonarthroscopic surgeons. Thus, there is a need for a better method of removing protruding tissue, but the prior art, considered as a whole, neither teaches nor suggests how the techniques of the prior art could be improved.

DISCOURSE OF THE INVENTION

The novel technique of this invention includes the pioneering method of debulking tissue by undermining the protruding part instead of attacking it directly. More particularly, where protruding tissue is pressing against a nerve, a cavity is formed in the tissue at the base of the protruding part, and a laser is employed to cause the cavity to collapse inwardly upon itself so that the protruding tissue falls into the cavity and thus disengages from the nerve.

In this manner, the protruding tissue is not directly attacked as in all known prior art methods. Significantly, the tissue that is cut out and removed is not immediately adjacent the nerve, thereby making the procedure safe and substantially reducing the risk of injuring the nerve.

A plurality of dilator tubes are used in the performance of the initial steps of the novel procedure, although the precise number of tubes used is not critical. For example, the initial step of the novel procedure may be advantageously conducted with four tubes in the following manner. The physician first selects the site of the incision and makes a small, arthroscopic incision at the selected site. A first or innermost tube having a small outer diameter is inserted through the incision to dilate the incision; said innermost tube is then telescopically received within a second tube having a slightly larger outside diameter that is next inserted to further dilate the incision. That second tube is in turn telescopically received within a third tube of still larger outer diameter that is inserted through the incision to dilate it still further and that third tube is telescopically received within a fourth or outermost tube that is inserted to fully dilate the incision. The innermost dilator tube is then removed and a first tissue cutter of small diameter is introduced through the hollow bore of the second dilator tube. A small amount of tissue is cut by rotating that first cutter about its longitudinal axis; a hex key may be employed by the physician to facilitate rotation of said first cutter. Both the second dilator tube and the first cutter are then removed. A second cutter of slightly larger diameter is then introduced through the bore of the third tube and another, larger cut is made in the tissue with the aid of the hex key if needed; the second cutter and third tube are then removed. A third cutter, having a still larger diameter, is then introduced through the bore of the fourth tube; a third, still larger cut is made, again with the hex key if needed, and the third cutter is removed.

This sequential use of successively lager cutters enables the gradual cutting of larger and larger amounts of tissue in a location beneath, i.e., radially inward of, the protruding tissue. Once the cutting has been completed, the initial procedure is finished and the second procedure is performed.

The second procedure begins with the fourth dilator tube still in place; a tube key member is positioned in locking engagement to the fourth dilator tube at the surface of the patient's skin to hold the fourth dilator tube in position.

The second procedure is performed with a series of progressively larger forceps; where two forceps are used, the first forcep is smaller than the second and is employed to remove the tissue cut in the performance of the initial step of the procedure. The first forcep is inserted through the fourth dilator tube and the physician squeezes the grip part of the forceps to capture cut tissue in the jaws of the forceps.

The first forceps is then withdrawn and the second, larger forceps is then inserted to complete the removal of tissue from the cavity. Still larger forceps may also be used to remove tissue as needed, i.e., this invention is not limited to any particular number of forceps.

The forceps, preferably, are of the type having a suction port to enable continuous removal of tissue from the cavity so that the forceps need not be removed after making each "bite" of tissue.

In the next step of the process, a solid impactor tool is introduced through the bore of the fourth dilator tube and said tool is hammered to compact the bonespur.

A laser is employed in the final step. It is inserted through the fourth dilator tube and its light is played over the inner disc material of the cavity; the extreme heat of the lightbeam causes the cavity to collapse, and the protruding tissue is vaporized in the cavity. In this manner, the pressure on the nerve is removed without directly abrading the tissue that pinched it, even if the protruding tissue does not fall into the cavity.

The steps of the novel method are performed with the novel tools just described, and said tools are grouped together to form a novel kit; the kit enhances the utility of the tools and aids the physician in the performance of the surgery.

It is an important object of this invention to advance the art of surgery in general and the art of arthroscopic surgery in particular by disclosing a heretofore unknown method of removing protruding tissue.

Another object is to provide in kit form the tools needed to perform the novel technique.

These and other objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

Similar reference numerals refer to similar parts throughout the several views of the drawings.

BEST MODES FOR CARRYING OUT THE INVENTION

Figure 1:
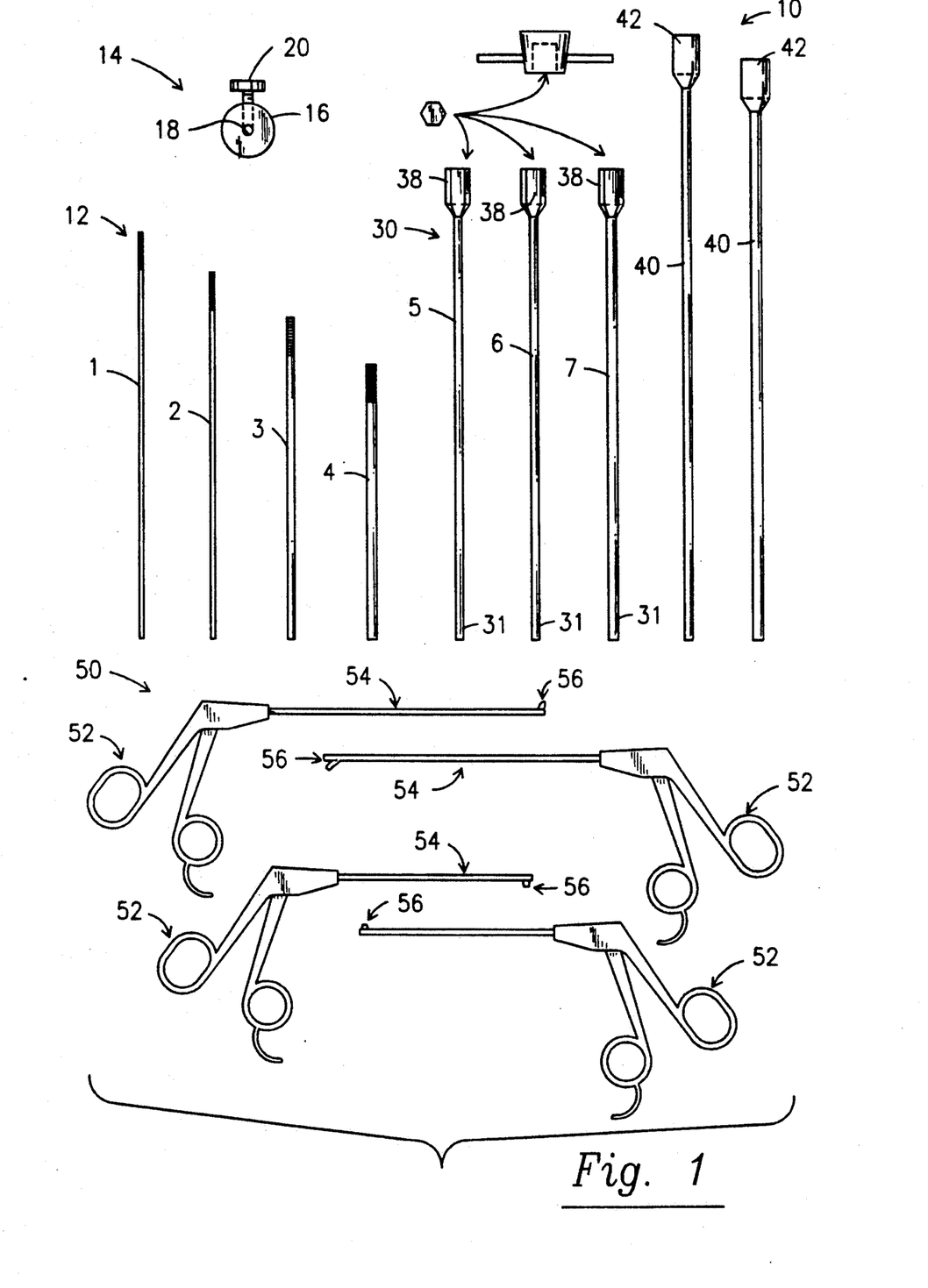
FIG. 1 is a plan view of the novel kit.

Referring first to FIG. 1, it will there be seen that the novel kit and novel tools contained therein are denoted as a whole by the reference numeral 10.

Kit 10 includes a plurality of hollow dilator tubes, collectively denoted 12; the tubular members are individually denoted 1, 2, 3, and 4 to indicate their order of use in the novel procedure. Tube 1 has the smallest inside and outside diameter, tube 2 has an inside and outside diameter slightly greater than that of tube 1, and so on. Tube 2 telescopically receives tube 1 and is telescopically received by tube 3 which in turn is telescopically received within tube 4 when the surgical procedure is initiated.

Figure 5:
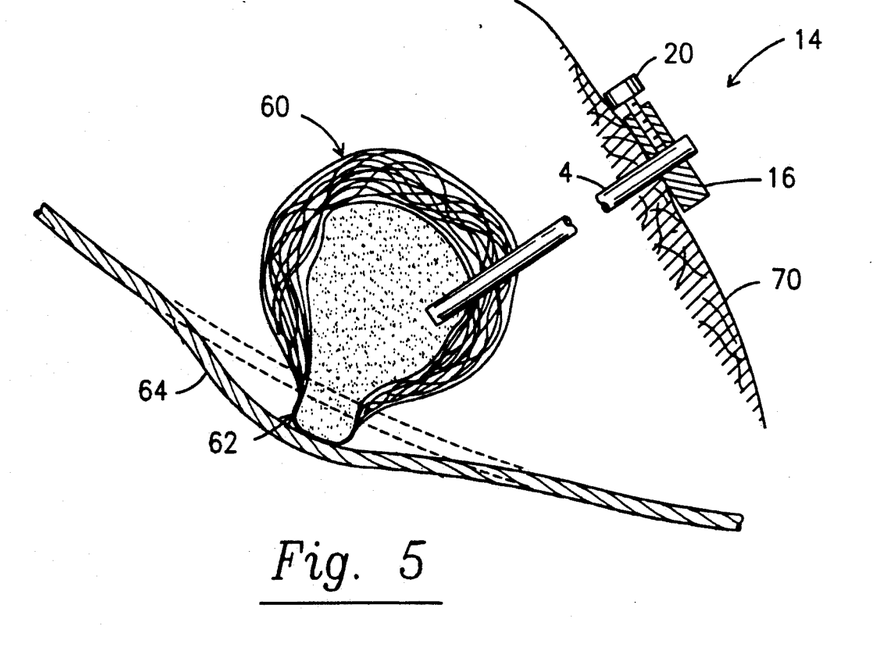
FIG. 5 is a sectional view showing how the largest dilator tube is held in place during the tissue-removal stage of the surgical procedure.

Tube key 14 includes disc 16, central aperture 18 and set screw 20 that is screw threadedly received within a radial bore. Aperture 18 slidably receives tube 4 and set screw 20 holds said tube 4 against axial movement as depicted in FIG. 5 when said screw is advanced so that its radially innermost end bears against said tube 4 at the appropriate step in the novel procedure.

The reference numeral 30 denotes the cutters as a whole, and the individual cutters are denoted 5, 6, and 7. Cutter 6 is a little larger in diameter than cutter 5 and a little smaller in diameter than cutter 7; all of the cutters are hollow tubular members and are sharpened at their respective distal ends, collectively denoted 31.

Hex key 32 includes a cylindrical central body part 34 and a diametrically extending rigid bar 36; part 34 is hollow and is specifically configured and dimensioned to slidingly receive and engage the complementally formed head or proximal end 38 of each cutter 5, 6, or 7. The head 38 of each cutter is the same size as the head of the other cutters so that one hex key 32 fits all of them. Bar 36 is rotated by the physician to achieve simultaneous and corresponding rotation of the particular cutter in use.

Figure 7:
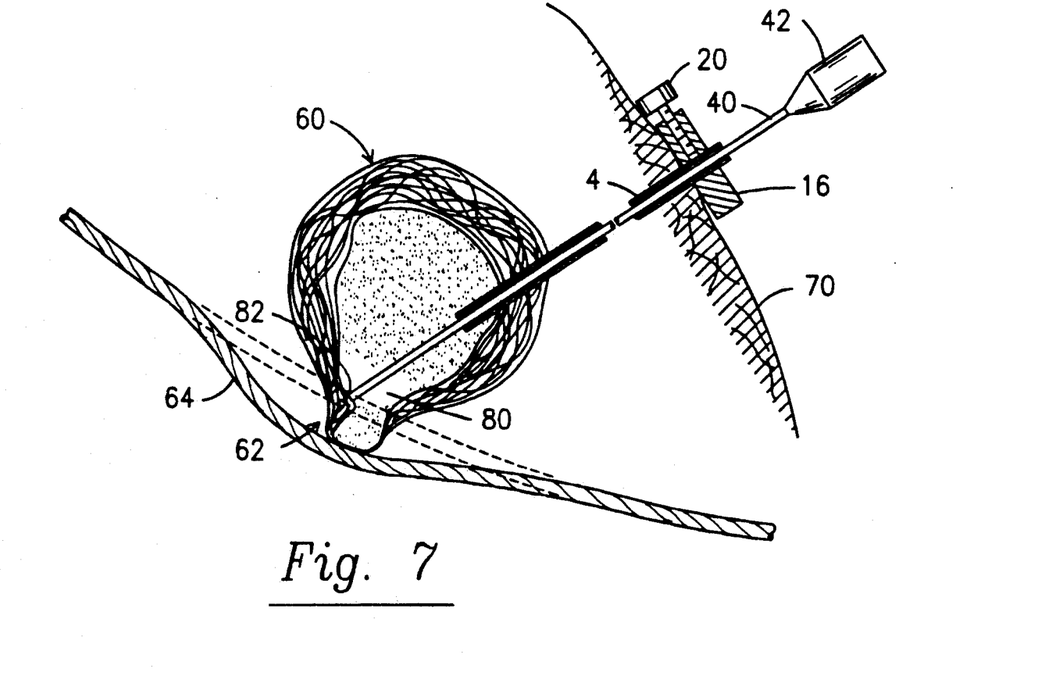
FIG. 7 is a sectional view of the same tissue after a cavity of the desired size has been formed below the bulge, and depicts an arthroscopic impactor tool in use to compact the bone that forms the peripheral walls of the cavity.

Kit 10 also includes a pair of impactors, collectively denoted 40. Each impactor 40 is a solid rod member having an enlarged impact head 42 at its proximal end; a hammer is employed by the physician to impact against head 42 when the impactor tool is in use as depicted in FIG. 7.

The forceps of this invention are collectively denoted 50; like the dilator tubes 12 and the cutters 30, no two of the forceps share the same size and they may be grouped such that the first member of the group is smaller than the second and so on. Each forcep member 50 includes a grip part 52, a neck or elongate part 54, and a jaw part 56 at the distal end of elongate part 54; note that the respective elongate parts of the tools also differ in length. A bias means holds jaws 56 in their open position when the tool is in its equilibrium or repose condition; the physician must squeeze the grip part 52 to close the jaws 56 so that a previously cut piece of tissue may be removed from the operation site.

Figure 2:
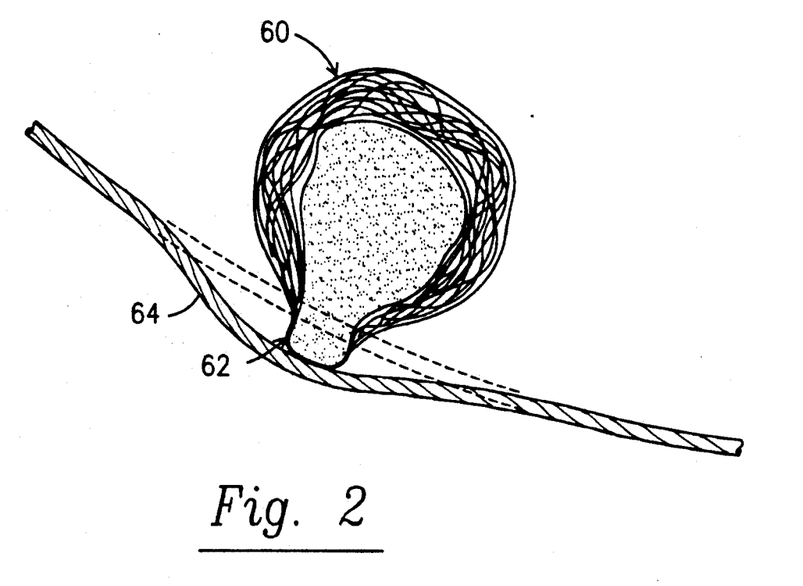
FIG. 2 is a sectional view of a tissue having a bulge that is bearing against and displacing a nerve from its natural position.

Having described the novel kit 10 and its contents, the steps of the novel procedure can now be easily described. In FIG. 2, tissue 60 requires debulking because it includes bulge 62 that protrudes outwardly from tissue 60 as its name implies and said bulge bears against and displaces nerve 64 from its natural position; the natural position of said nerve is denoted in phantom lines in FIG. 2.

Figure 3:
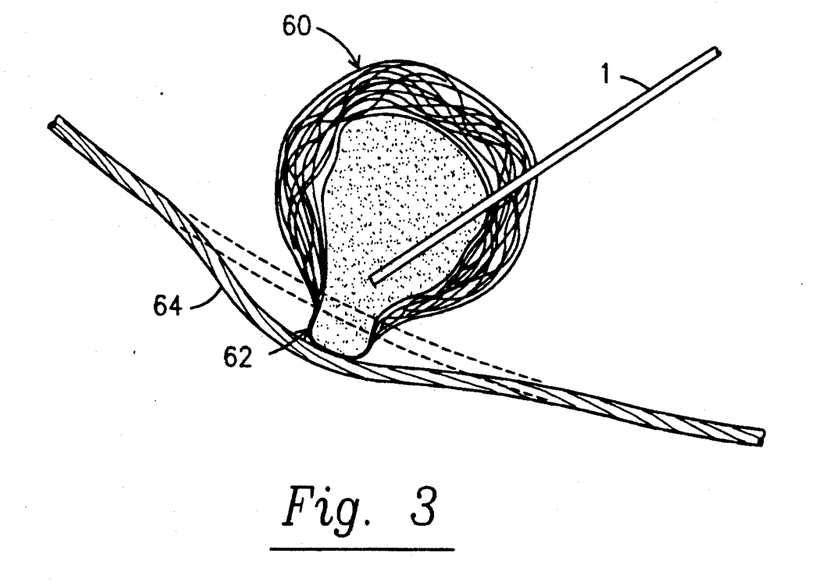
FIG. 3 is a sectional view showing the insertion of a first dilator tube through the arthroscopic incision.

After an arthroscopic incision is formed at a carefully selected site, dilator tube 1 is inserted therethrough as depicted in FIG. 3; this is followed by the successive insertion of dilator tubes 2, 3, and 4 in telescopically receiving relation to one another so that the incision is successively dilated.

Figure 4:
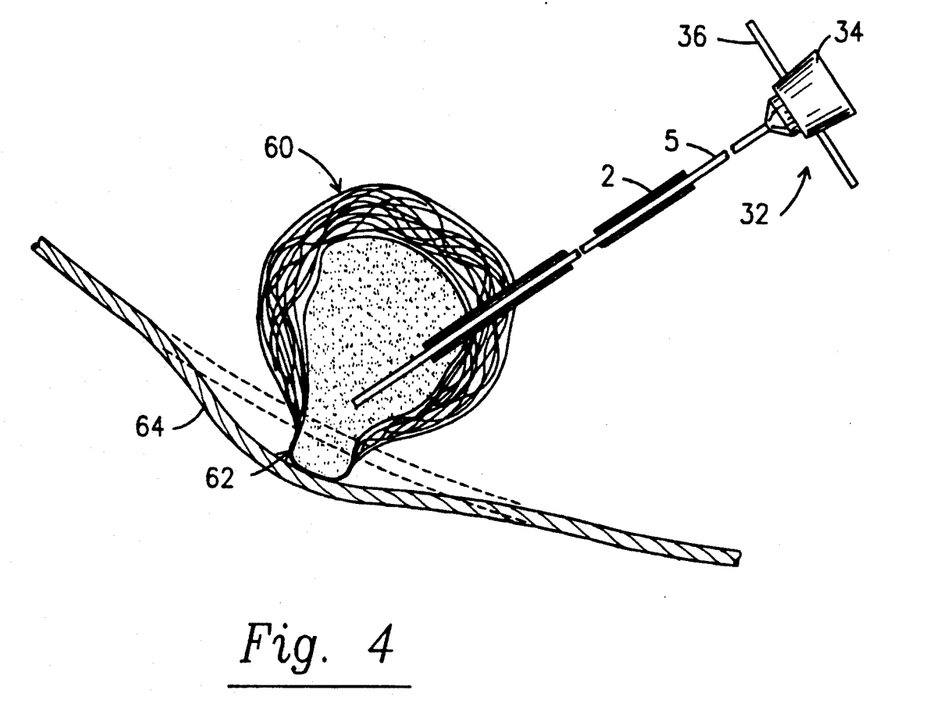
FIG. 4 is a sectional view showing the use of an arthroscopic cutting tool to cut tissue below the base of the protruding part of the tissue.

Dilator tube 1 is then removed and the first cutter 5 is inserted through the bore of dilator tube 2 as depicted in FIG. 4; hex key 32 is employed, if desired, to rotate the cutter to achieve the desired cut. Dilator tubes 3 and 4 are not shown in FIG. 4 to simplify the drawing. Dilator tube 2 and cutter 5 are then withdrawn and second cutter 6 is inserted through the hollow bore of dilator tube 3 and a third, larger out is made; tube 3 and cutter 6 are then withdrawn and third cutter 7 is inserted through the hollow bore of tube 4 to make a still further cut. This completes the initial step of the procedure and third cutter 7 is withdrawn, but the fourth dilator tube 4 is left in place.

Tube key 14 is then positioned in looking engagement to tube 4 as depicted in FIG. 5 to hold said tube into the depicted position when screw 20 is advanced as mentioned earlier. Note that tube key 14 is disposed in abutting, overlying relation to the patient's skin 70; this arrangement prevents axial travel of tube 4 when suitable means are employed to secure tube key 14 into said abutting relation to skin 70.

Figure 6:
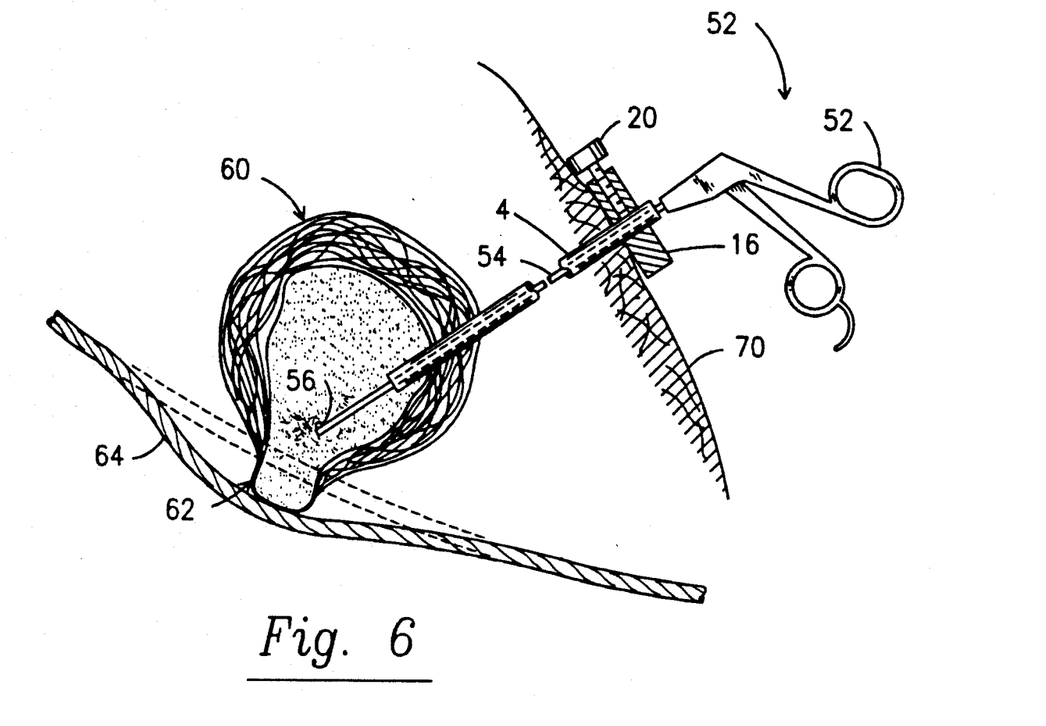
FIG. 6 is a sectional view showing the use of an arthroscopic forceps to remove tissue cut in the manner depicted in FIG. 4.

The smallest of the forceps 50 is then inserted through the bore of tube 4, as depicted in FIG. 6, and the physician squeezes the grip 52 to seize a cut piece of tissue. Where a common forceps is used, the physician must withdraw the forceps after each bite to deposit the removed tissue at a suitable collection site; thus, multiple re-entries to the operation site must be made. Accordingly, a forceps having a suction port for the continuous removal of excised tissue is the tool of choice so that only one entry per forceps need be made. After tissue has been removed with the smallest forceps, the process is repeated with successively larger forceps until the cavity 80 depicted in FIG. 7 has been completed. Note that cavity 80 is radially inwardly of bulge 62 and that it separates said bulge from the rest of the tissue.

FIG. 7 also depicts impactor tool 40 which is employed to compact the bonespur 82 that forms the walls of the cavity 80. The physician hammers the enlarged end 42 of the impactor 40 until satisfied that all loose fragments have been compacted.

Figure 8:
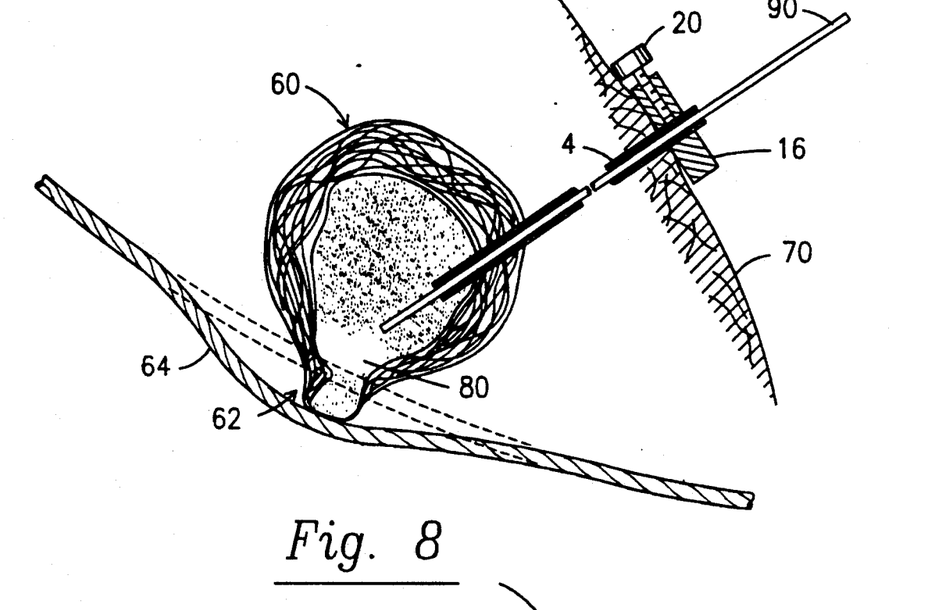
FIG. 8 is a sectional view of the same tissue after the impactor tool has been used, and depicts an arthroscopic laser treating the exposed walls of the cavity.
Figure 9:
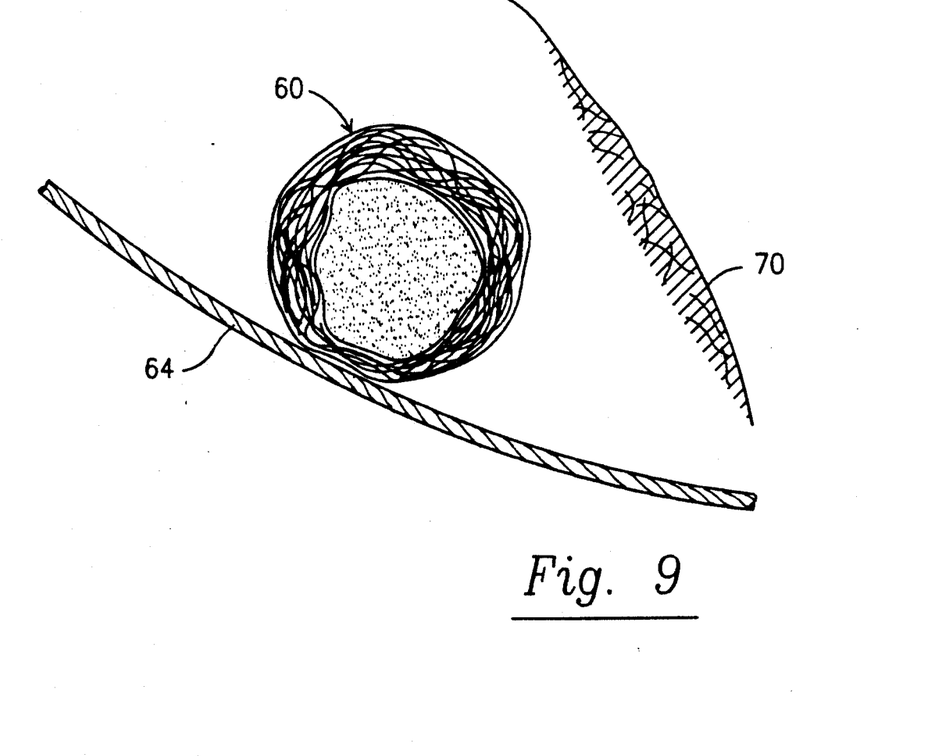
FIG. 9 is a sectional view of the same tissue after the protruding tissue has collapsed into the cavity and the nerve has returned to its initial position.

Laser 90 is then inserted through tube 4 as depicted in FIG. 8 and the heat generated thereby heats the inner disc material and thereby causes the collapse of cavity 80 as depicted in FIG. 9; advantageously, since cavity 80 undermines the protruding tissue 62, the cavity is filled with said protruding tissue as a part of the collapsing process. Nerve 64 returns to its normal position as depicted in FIG. 9 and the discomfort experienced by the patient is ended.

This highly novel procedure is performed away from the nerve and is thus safer than the procedures heretofore known. Just as importantly, it is at least equally effective. The procedure has been described by making reference to hand-powered tools, but motorized implements could be used as well and most surgeons will prefer to use motorized cutters. The laser could be employed to form the cavity 82 instead of just to collapse it, but the forming of the cavity by hand is preferred over the use of a laser; use of a laser to form the cavity could be dangerous.

This invention is clearly new and useful. Moreover, it was not obvious to those of ordinary skill in this art at the time it was made, in view of the prior art when considered as a whole in accordance with the requirements of law.

This invention pioneers the art of tissue debulking by undermining the offending tissue. Accordingly, as a matter of law, the claims that follow are entitled to broad interpretation so as to protect from piracy the heart or essence of this breakthrough invention.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method for removing a protruding tissue from abutting engagement with a nerve, comprising the steps of:

undermining tissue, which protrudes into abutting engagement with a nerve, by forming a cavity adjacent said tissue;

performing said undermining with arthroscopic tools;

employing progressively larger dilator tubes and progressively larger cutter tubes to enlarge the cavity;

dimensioning the cavity so that it has a volume adequate to fully receive therewithin the protruding tissue; and inducing the collapse of the cavity by using a laser means to heat inner disc material of the cavity so that the producing tissue falls into said cavity and out of engagement with said nerve.

2. The method of claim 1, wherein the step of undermining said protruding tissue includes the step of making an arthroscopic incision at a preselected operation site and inserting a first dilator tube into said incision.

3. The method of claim 2, further comprising the step of inserting successively larger in diameter dilator tube members into said incision while the smaller in diameter tubes remain in said incision so that as said incision is successively dilated, each successive dilator tube telescopically receives its preceding dilator tube.

4. The method of claim 2, wherein the step of undermining said protruding tissue further includes the step of inserting into said incision a second dilator tube having an outer diameter greater than the outer diameter of the first dilator tube while said first dilator tube remains in said incision, said second dilator tube telescopically receiving said first dilator tube.

5. The method of claim 4, wherein the step of undermining further includes the step of inserting into said incision a third dilator tube having an outer diameter greater than the outer diameter of said second dilator tube while said first and second dilator tubes remain in said incision, said third dilator tube telescopically receiving said second dilator tube.

6. The method of claim 5, wherein the step of undermining further includes the step of inserting into said incision a fourth dilator tube having an outer diameter greater than the outer diameter of said third dilator tube while said first, second and third dilators tubes remain in said incision, said fourth dilator tube telescopically receiving said third dilator tube.

7. The method of claim 6, further comprising the steps of withdrawing said first dilator tube from said incision, inserting a first cutter member through the bore of said second dilator tube, and cutting a piece of tissue by rotating said first cutter member about its longitudinal axis.

8. The method of claim 7, further comprising the steps of withdrawing said first cutter member and said second dilator tube, inserting a second cutter member having a diameter larger than said first cutter member through the bore of said third dilator tube, and cutting a larger piece of tissue by rotating said second cutter member about its longitudinal axis.

9. The method of claim 8, further comprising the steps of withdrawing said second cutter member and said third dilator tube, inserting a third, larger in diameter cutter member through the bore of said fourth dilator tube, and cutting a still larger piece of tissue by rotating said third cutter member about its longitudinal axis.

10. The method of claim 9, further comprising the step of securing said fourth dilator tube with a tube key member that abuts the surface of the patient's skin and which holds the fourth dilator tube against axial displacement.

11. The method of claim 10, further comprising the step of inserting a first forceps through the bore of said fourth dilator tube and removing excised tissue with said forceps.

12. The method of claim 11, further comprising the step of inserting through the bore of said fourth dilator tube a second forceps of larger size than said first forceps and removing still larger pieces of excised tissue with said second forceps.

13. The method of claim 12, further comprising the step of compacting bone that forms the peripheral walls of said cavity by inserting an impactor member into said cavity through the bore of said fourth dilator tube and hammering said impactor member as needed.

14. The method of claim 13, further comprising the step of inserting a laser into said cavity through the bore of said fourth dilator tube and activating said laser to heat inner disc material of the cavity to a temperature sufficient to cause the collapse of said cavity and the concomitant reception thereinto of said protruding tissue.

* * * * *

EX PARTE REEXAMINATION CERTIFICATE (7813th)
United States Patent
Bonati (10) Number: US 5,241,972 C1
(45) Certificate Issued: Oct. 19, 2010

(54) METHOD FOR DEBULKING TISSUE TO REMOVE PRESSURE ON A NERVE

(75) Inventor: Alfred O. Bonati, New Port Richey, FL (US)

(73) Assignee: AOB Properties Limited Partnership, Hudson, FL (US)

Reexamination Request:
No. 90/009,563, Aug. 19, 2009

Reexamination Certificate for:
Patent No.: 5,241,972
Issued: Sep. 7, 1993
Appl. No.: 07/695,633
Filed: May 3, 1991

(51) Int. Cl.
A61B 19/00 (2006.01)
A61B 17/00 (2006.01)

(52) U.S. Cl. .............................. 128/898; 606/2; 606/53; 606/13

(58) Field of Classification Search .......................... None
See application file for complete search history.

(56) References Cited

U.S. PATENT DOCUMENTS 4,610,665 A * 9/1986 Matsumoto et al.

OTHER PUBLICATIONS

Kambin, Arthroscopic Microdiscectomy: Minimal Intervention in Spinal Surgery, Urban & Schwartzenberg pp. 67–141 (Jan. 1991).*

Hijikata, Percutaneous Nucleotomy A New Concept Technique and 12 Years' Experience, Clinical Orthopedics and Related Research, vol. 238, pp. 9–23 (1989).*

* cited by examiner

Primary Examiner—Beverly M. Flanagan (57) ABSTRACT

An arthroscopic method for debulking tissue and a kit of arthroscopic tools for performing the steps of the method. A protruding piece of tissue that is bearing against a nerve is undetermined by the formation of a cavity beneath it, and the cavity is collapsed by heat generated by a laser. When the cavity collapses, the protruding tissue falls into it and separates from the nerve. The kit includes plural dilator tubes that are used to progressively dilate the arthroscopic incision and plural cutter tubes that are used in sequence to cut larger and larger pieces of tissue. Plural forceps are employed to remove the cut tissue to form the cavity, and impactor members in the kit are used to compact the bone that surrounds the cavity just before the laser is introduced into the cavity to collapse it.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-14 is confirmed.

* * * * *